(12) United States Patent
Masuda

(10) Patent No.: US 10,386,343 B2
(45) Date of Patent: Aug. 20, 2019

(54) GAS CHROMATOGRAPH

(71) Applicant: Shimadzu Corporation, Kyoto (JP)

(72) Inventor: Shingo Masuda, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 154 days.

(21) Appl. No.: 15/815,039

(22) Filed: Nov. 16, 2017

(65) Prior Publication Data

US 2019/0145941 A1    May 16, 2019

(51) Int. Cl.
| | |
|---|---|
| *B01D 53/02* | (2006.01) |
| *G01N 30/26* | (2006.01) |
| *G05D 7/06* | (2006.01) |
| *G01N 30/68* | (2006.01) |
| G01N 30/60 | (2006.01) |
| G01N 30/02 | (2006.01) |

(52) U.S. Cl.
CPC .............. *G01N 30/26* (2013.01); *G01N 30/68* (2013.01); *G05D 7/06* (2013.01); *G01N 2030/025* (2013.01); *G01N 2030/6013* (2013.01)

(58) Field of Classification Search
CPC .......... G01D 30/26; G01D 30/68; G05D 7/06; G01N 2030/25; G01N 2030/6013
See application file for complete search history.

(56) References Cited

U.S. PATENT DOCUMENTS

| | | | | |
|---|---|---|---|---|
| 7,468,095 | B2 * | 12/2008 | Tipler | G01N 30/32 73/23.42 |
| 8,656,754 | B2 * | 2/2014 | Kawana | G01N 30/28 73/23.36 |
| 9,983,104 | B2 * | 5/2018 | Tipler | G01N 1/2226 |
| 2006/0288803 | A1 * | 12/2006 | Weissgerber | G01N 30/36 73/865.8 |
| 2008/0105119 | A1 * | 5/2008 | Arnold | G01N 30/54 95/18 |
| 2011/0259451 | A1 * | 10/2011 | Weissgerber | G01N 30/36 137/565.11 |
| 2014/0250978 | A1 * | 9/2014 | McCauley | G01N 30/16 73/23.39 |
| 2014/0318224 | A1 * | 10/2014 | Onoda | F04B 23/06 73/61.56 |
| 2015/0059439 | A1 * | 3/2015 | Tipler | G01N 30/72 73/23.37 |
| 2015/0346167 | A1 * | 12/2015 | Terai | G01N 30/32 73/23.41 |

\* cited by examiner

*Primary Examiner* — Christopher P Jones
(74) *Attorney, Agent, or Firm* — Maier & Maier, PLLC

(57) ABSTRACT

When a flow rate of a carrier gas calculated by a column flow rate calculation unit is controlled to be a first flow rate, and when the flow rate of the carrier gas is controlled to be a second flow rate, the flow rates of the carrier gas are detected by a whole flow rate detection unit, and a gas leakage determination unit determines of leakage of the carrier gas on the basis of the rates. Since the flow rate of the carrier gas is changed and the detected value of the whole flow rate detection unit is used at different flow rates, a case can be discriminated where an offset occurs in the detected value of the whole flow rate detection unit and a case where leakage of the carrier gas occurs. Thus, it is satisfactorily determined the presence or absence of the leakage of the carrier gas.

8 Claims, 7 Drawing Sheets

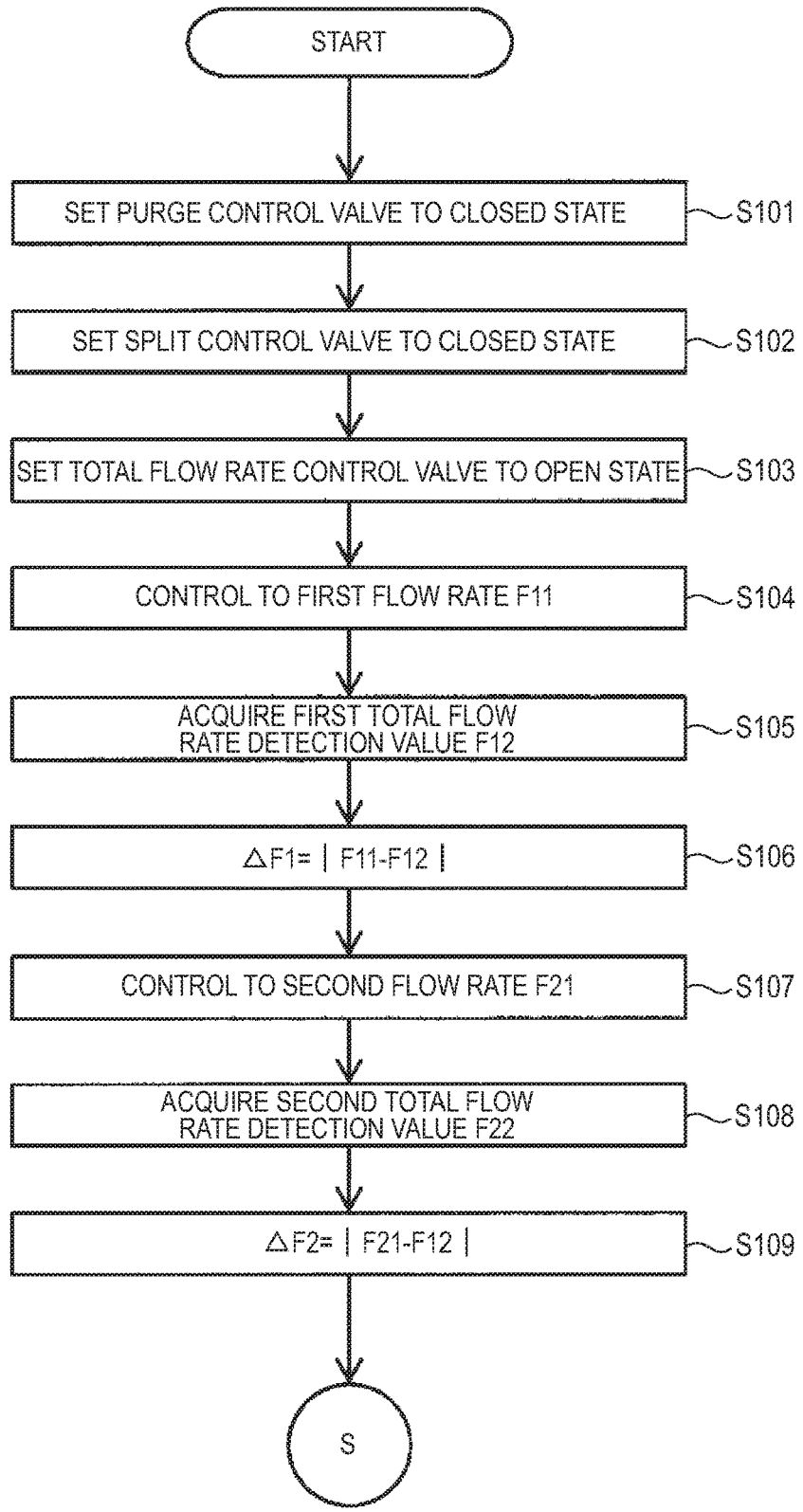

GAS CHROMATOGRAPH

BACKGROUND OF THE INVENTION

Field of the Invention

The present invention relates to a gas chromatograph for performing analysis by supplying a sample and a carrier gas into a column.

Description of the Related Art

In a gas chromatograph, the sample and the carrier gas are supplied into the column, and each component in the sample is separated in a process in which the carrier gas passes through the column. The carrier gas is supplied from the gas supply flow path to a sample introduction unit and mixed with the sample in the sample introduction unit, and then, the carrier gas is introduced into the column from a column inlet. As a method for introducing the sample into the column from the column inlet, a split introduction method, a whole amount introduction method and the like are known (See, for example, JP-A-2014-215195 to be described below).

When performing the analysis, the flow rate of the carrier gas passing through the column (hereinafter referred to as "column flow rate") is used in various modes. For example, when the sample is introduced into the column from the column inlet by the split introduction method, the amount of the sample flowing in the column depends on a split ratio determined on the basis of a ratio between the whole flow rate of the carrier gas supplied to the sample introduction unit and the column flow rate. Therefore, unless the column flow rate can be accurately grasped, it is not possible to accurately grasp the amount of the sample flowing in the column, which may affect a quantitative value to be measured.

In addition, although the degree of separation of the sample components in the column depends on the linear velocity of the carrier gas passing through the column, the linear velocity is calculated from the column flow rate, the column size, and the like. Therefore, unless the column flow rate can be accurately grasped, it is not also possible to accurately grasp the linear velocity, and a desired separation may not be obtained. In this way, the column flow rate is an important parameter when performing the analysis, and it is required to accurately grasp the column flow rate.

However, it is usually difficult to measure the column flow rate to obtain the actual measurement value. Therefore, a method for detecting the pressure of the carrier gas at the column inlet (hereinafter referred to as "column inlet pressure") and calculating the column flow rate on the basis of the column inlet pressure is generally performed. When calculating the column flow rate, setting values concerning columns such as an inner diameter and a length of the column and a film thickness of the liquid phase, the temperature of the column, and the like are used in addition to the column inlet pressure.

The setting values concerning the columns are set when the operator performs the input operation. However, in some cases, the operator mistakes the type of column to be mounted on the gas chromatograph or the mounting method, or the user inputs a setting value different from the type of the actually mounted column. In such cases, it is not possible to calculate an accurate column flow rate, and various adverse effects as described above may occur.

Therefore, JP-A-2014-215195 suggests a structure in which it is determined whether or not the calculated column flow rate is an accurate value, by calculating the flow rate of the carrier gas passing through the column, and by comparing the calculated column flow rate with the actual whole flow rate of the carrier gas detected by the whole flow rate detection unit.

However, even when the operator does not mistake the type of column to be mounted on the gas chromatograph or the mounting method, or even when the operator does not input a setting value different from the type of the actually mounted column, there is case where the calculated column flow rate (hereinafter referred to as "column flow rate calculation value") does not coincide with the whole flow rate of the carrier gas detected by the whole flow rate detection unit (hereinafter referred to as "whole flow rate detection value"). As a cause thereof, for example, an offset may occur in the whole flow rate detection value on the basis of a change in the supply pressure of the carrier gas or the air temperature, or leakage of the carrier gas may occur in the flow path from the whole flow rate detection unit to the sample introduction unit.

FIGS. 6A and 6B are diagrams for describing a relation between the column flow rate calculation value and the whole flow rate detection value. FIG. 6A illustrates a case where leakage of the carrier gas occurs, and FIG. 6B illustrates a case where an offset occurs in the whole flow rate detection value.

As illustrated in FIG. 6A, in a case where the leakage of the carrier gas occurs in the flow path from the whole flow rate detection unit to the sample introduction unit, if the flow rate of the carrier gas is large, the leakage amount relative to the flow rate of the carrier gas also becomes relatively large. Therefore, as the column inlet pressure is high, the difference between the whole flow rate detection value and the column flow rate calculation value becomes large. That is, when a difference A1 between the whole flow rate detection value and the column flow rate calculation value at a column inlet pressure $P_H$ is compared with a difference A2 between the whole flow rate detection value and the column flow rate calculation value at a column inlet pressure $P_L$ lower than the column inlet pressure $P_H$, the difference A1 becomes larger than the difference A2.

Meanwhile, as illustrated in FIG. 6B, when an offset occurs in the whole flow rate detection value, the offset amount of the whole flow rate detection value with respect to the column flow rate calculation value is substantially constant, irrespective of the flow rate of the carrier gas. That is, the difference B1 between the whole flow rate detection value and the column flow rate calculation value at the column inlet pressure $P_H$, and the difference B2 between the whole flow rate detection value and the column flow rate calculation value at the column inlet pressure $P_L$ lower than the column inlet pressure $P_H$ are almost the same value.

Therefore, when the flow rate of the carrier gas is high, it is possible to easily discriminate the cause of the inconsistency between the column flow rate calculation value and the whole flow rate detection value. For example, since the difference A1 of FIG. 6A and the difference B1 of FIG. 6B at the column inlet pressure $P_H$ are largely different from each other, simply by comparing the column flow rate calculation value and the whole flow rate detection value at the column inlet pressure $P_L$ with the threshold values, it is possible to easily discriminate whether the cause of inconsistency between the values is due to the occurrence of the leakage of the carrier gas or the occurrence of the offset in the whole flow rate detection value.

However, when the flow rate of the carrier gas is small, it is difficult to discriminate the cause of the inconsistency between the column flow rate calculation value and the whole flow rate detection value. For example, since the difference A2 of FIG. 6A and the difference B2 of FIG. 6B at the column inlet pressure $P_L$ are substantially the same value, by merely comparing the column flow rate calculation value and the whole flow rate detection value at the column inlet pressure $P_L$ with the threshold value, it is difficult to determine whether the cause of inconsistency between the values is due to the occurrence of leakage of the carrier gas or due to the occurrence of the offset in the whole flow rate detection value.

When the inner diameter of the flow path from the whole flow rate detection unit to the sample introduction unit is small or when the flow path is long, since the resistance at the time of flowing of the carrier gas becomes large, there is no choice but to reduce the flow rate of the carrier gas. Also, even when performing the analysis using a flammable gas such as hydrogen, in some cases, there is no choice but to reduce the flow rate of the carrier gas in view of safety. In such a case, in the conventional configuration, since it is not possible to specify the reason why the column flow rate calculation value and the whole flow rate detection value do not coincide with each other, it was difficult to determine the presence or absence of the leakage of the carrier gas, using the column flow rate calculation value and the whole flow rate detection value.

SUMMARY OF THE INVENTION

The invention has been made in view of the above circumstances, and an object thereof is to provide a gas chromatograph capable of satisfactorily determining the presence or absence of leakage of a carrier gas.

The gas chromatograph according to the invention includes a column, a sample introduction unit, a gas supply unit, a whole flow rate detection unit, a pressure detection unit, a column flow rate calculation unit, a first flow rate control unit, a second flow rate control unit, and a gas leakage determination unit. The sample is introduced into the column from a column inlet. The sample introduction unit introduces the sample together with the carrier gas into the column from the column inlet. The gas supply unit communicates with the sample introduction unit to supply the carrier gas to the sample introduction unit. The whole flow rate detection unit detects the flow rate of the carrier gas supplied from the gas supply unit. The pressure detection unit detects the pressure of the carrier gas at the column inlet. The column flow rate calculation unit calculates the flow rate of the carrier gas passing through the column, on the basis of the pressure of the carrier gas at the column inlet. The first flow rate control unit controls the flow rate of the carrier gas supplied from the gas supply unit so that the flow rate of the carrier gas calculated by the column flow rate calculation unit becomes a first flow rate. The second flow rate control unit controls the flow rate of the carrier gas supplied from the gas supply unit so that the flow rate of the carrier gas calculated by the column flow rate calculation unit becomes a second flow rate different from the first flow rate. The gas leakage determination unit determines presence or absence of leakage of the carrier gas, on the basis of the flow rate of the carrier gas detected by the whole flow rate detection unit when the flow rate of the carrier gas is controlled by the first flow rate control unit, the flow rate of the carrier gas detected by the whole flow rate detection unit when the flow rate of the carrier gas is controlled by the second flow rate control unit, the first flow rate, and the second flow rate.

According to such a configuration, when the flow rate of the carrier gas calculated by the column flow rate calculation unit is controlled to be the first flow rate, and when the flow rate of the carrier gas is controlled to be the second flow rate, the flow rates of the carrier gas are detected by the whole flow rate detection unit, respectively, and the presence or absence of the leakage of the carrier gas is determined on the basis of the flow rates, the first flow rate, and the second flow rate. In this way, since the flow rate of the carrier gas changes and the detected value of the whole flow rate detection unit is used at different flow rates (the first flow rate and the second flow rate), it is possible to satisfactorily discriminate a case where an offset occurs in the detected value of the whole flow rate detection unit and a case where leakage of the carrier gas occurs. Thus, it is possible to satisfactorily determine the presence or absence of leakage of the carrier gas.

The gas leakage determination unit may include a first difference calculation unit, a second difference calculation unit, and a comparison processing unit. The first difference calculation unit calculates a difference between the flow rate of the carrier gas detected by the whole flow rate detection unit when the flow rate of the carrier gas is controlled by the first flow rate control unit and the first flow rate. The second difference calculation unit calculates a difference between the flow rate of the carrier gas detected by the whole flow rate detection unit when the flow rate of the carrier gas is controlled by the second flow rate control unit and the second flow rate. The comparison processing unit compares a difference between the difference calculated by the first difference calculation unit and the difference calculated by the second difference calculation unit with a first threshold value.

According to such a configuration, the flow rate of the carrier gas changes, the detected values of the whole flow rate detection unit at different flow rates (the first flow rate and the second flow rate) are acquired, and the difference between the detected value of the whole flow rate detection unit at the first flow rate and the first flow rate, and the difference between the detected value of the whole flow rate detection unit at the second flow rate and the second flow rate is calculated. When leakage of the carrier gas occurs, since the differences calculated thus are different values, by comparing the difference with the first threshold value, the presence or absence of leakage of the carrier gas can be satisfactorily determined.

The gas chromatograph may further include a first notification control unit which notifies the leakage, when the gas leakage determination unit determines that there is leakage of the carrier gas.

According to such a configuration, it is possible to notify the determination result after satisfactorily determining the presence or absence of leakage of the carrier gas. Therefore, the operator can satisfactorily check the presence or absence of leakage of the carrier gas by clearly distinguishing from a case where an offset occurs in the detected value of the whole flow rate detection unit.

The gas chromatograph may further include a detection abnormality determination unit which determines presence or absence of detection abnormality in the whole flow rate detection unit, by comparing the difference calculated by the first difference calculation unit or the second difference calculation unit with a second threshold value, when the gas leakage determination unit determines that there is no leakage of the carrier gas.

According to such a configuration, in a case where it is determined that there is no leakage of the carrier gas after a satisfactory determination of the presence or absence of the leakage of the carrier gas, by comparing the difference calculated by the first difference calculation unit or the second difference calculation unit with the second threshold value, the presence or absence of the detection abnormality in the whole flow rate detection unit. That is, when it is determined that there is no leakage of the carrier gas, if the difference calculated by the first difference calculation unit or the second difference calculation unit is large, there is a high possibility of the detection abnormality such as an occurrence of an offset in the detected value of the whole flow rate detection unit. Therefore, by comparing the difference with the second threshold value, it is possible to satisfactorily determine the presence or absence of the detection abnormality in the whole flow rate detection unit.

The gas chromatograph may further include a second notification control unit which notifies detection abnormality, when the detection abnormality determination unit determines that there is a detection abnormality in the whole flow rate detection unit.

According to such a configuration, it is possible to notify the result of the determination after satisfactorily determining the presence or absence of the detection abnormality in the whole flow rate detection unit. Therefore, the operator can satisfactorily check the detection abnormality such as the occurrence of the offset in the detected value of the whole flow rate detection unit, by clearly distinguishing from the case where the leakage of the carrier gas occurs.

According to the invention, since it is possible to satisfactorily distinguish between a case where an offset occurs in the detected value of the whole flow rate detection unit and a case where leakage of the carrier gas occurs, it is possible to satisfactorily determine the presence or absence of leakage of the carrier gas.

BRIEF DESCRIPTION OF THE DRAWINGS

FIG. 4A is a flowchart illustrating an example of a process performed by a control unit when executing a whole amount supply mode of gas;

DETAILED DESCRIPTION OF THE INVENTION

Figure 1:
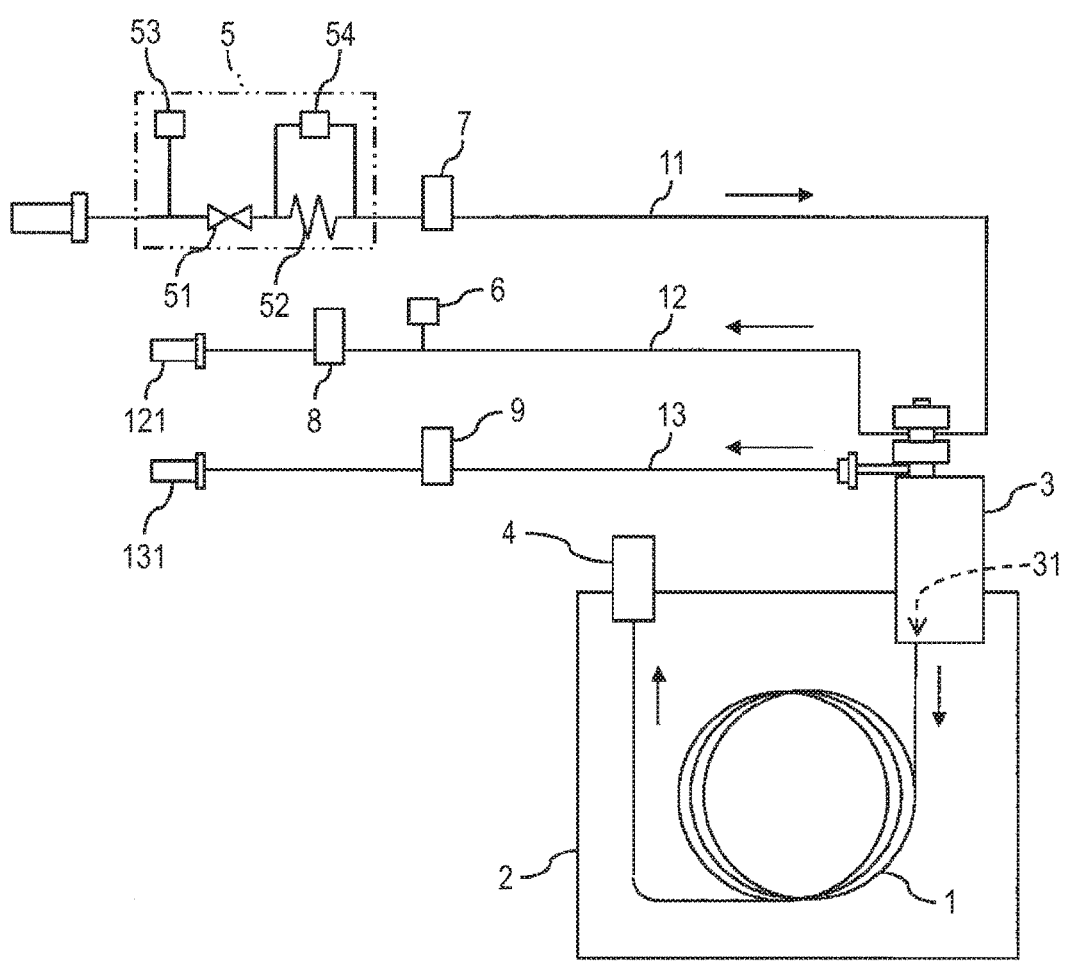
FIG. 1 is a schematic view illustrating a configuration example of a gas chromatograph according to an embodiment of the invention.

FIG. 1 is a schematic view illustrating a configuration example of a gas chromatograph according to an embodiment of the invention. The gas chromatograph performs an analysis by supplying a sample and a carrier gas into a column 1, and includes a column oven 2, a sample introduction unit 3, a detector 4, a whole flow rate detection unit 5, a pressure detection unit 6, a whole flow rate control valve 7, a purge control valve 8, a split control valve 9, and the like, in addition to the column 1.

The column 1 includes, for example, a capillary column and is heated in the column oven 2 during analysis. The carrier gas is supplied into the column 1 together with the sample from the sample introduction unit 3 via a column inlet 31. Each component in the sample is separated in the process of passing through the column 1 and is detected by the detector 4. The detector 4 can be made up of various detectors such as, for example, a flame ionization detector (FID).

The sample introduction unit 3 introduces the carrier gas into the column 1 from the column inlet 31, and, for example, a sample vaporization chamber (not illustrated) is formed therein. In the sample vaporization chamber, a liquid sample is injected, and a sample vaporized in the sample vaporization chamber and the carrier gas are introduced into the column 1 from the column inlet 31. A gas supply flow path 11, a purge flow path 12, a split flow path 13, and the like communicate with the sample vaporization chamber.

The gas supply flow path 11 communicates with the sample vaporization chamber of the sample introduction unit 3, and constitutes a gas supply unit for supplying the carrier gas to the sample vaporization chamber. The purge flow path 12 is a flow path for discharging undesirable components generated from a septum or the like to the outside from the purge vent 121. The split flow path 13 is a flow path for discharging extra sample components together with the carrier gas from the split vent 131 to the outside, when the carrier gas is introduced into the column 1 from the column inlet 31 by the split introduction method.

The whole flow rate detection unit 5 is provided in the gas supply flow path 11 to detect the flow rate (whole flow rate) of the carrier gas supplied from the gas supply flow path 11 to the sample introduction unit 3. For example, a valve 51, a resistor 52, a first pressure sensor 53, a second pressure sensor 54, and the like are provided in the whole flow rate detection unit 5. The valve 51 is provided in the gas supply flow path 11 to open and close the gas supply flow path 11. The resistor 52 is provided on the downstream side of the valve 51 in the gas supply flow path 11 to impart resistance to the carrier gas flowing in the gas supply flow path 11.

The first pressure sensor 53 detects the pressure (supply pressure) of the carrier gas flowing on the upstream side of the valve 51. Meanwhile, the second pressure sensor 54 detects the differential pressure of the carrier gas on the upstream side and the downstream side of the resistor 52. In the whole flow rate detection unit 5, the whole flow rate of the carrier gas is detected on the basis of the pressure detected by the first pressure sensor 53 and the second pressure sensor 54. In the whole flow rate detection unit 5 having such a configuration, there is a case where an offset occurs in the whole flow rate (whole flow rate detection value) of the detected carrier gas, on the basis of the change in the supply pressure of the carrier gas or the air temperature.

The pressure detection unit 6 is made up of, for example, a pressure sensor provided in the purge flow path 12, and detects the pressure (column inlet pressure) of the carrier gas at the column inlet 31. The pressure detection unit 6 may be provided in any other portion (for example, the split flow path 13 or the like) communicating with the column inlet 31, without being limited to the purge flow path 12. However, since the pressure loss is hard to occur due to the characteristics such as the small flow rate of the gas and flowing of gas at a substantially constant flow rate, by providing the pressure detection unit 6 in the purge flow path 12, the column inlet pressure can be more accurately detected.

By opening and closing the gas supply flow path 11, the whole flow rate control valve 7 can adjust the flow rate of the supplied carrier gas, between an open state in which the carrier gas is supplied from the gas supply flow path 11 to the sample introduction unit 3, and a closed state in which the supply of the carrier gas is stopped. The purge control valve 8 can adjust the gas discharge amount between the open state in which the gas is discharged from the purge flow path 12 to the outside and the closed state in which the gas is not discharged, by opening and closing the purge flow path 12. The split control valve 9 can adjust the gas discharge amount between the open state in which the gas is discharged from the split flow path 13 to the outside and the closed state in which the gas is not discharged, by opening and closing the split flow path 13.

The purge flow path 12 and the split flow path 13 constitute a gas discharge flow path for discharging a part of the gas in the sample introduction unit 3 during analysis. That is, during the analysis, when the whole flow rate control valve 7, the purge control valve 8, and the split control valve 9 are in the open state, a part of the gas in the sample introduction unit 3 is discharged from the purge flow path 12 and the split flow path 13. The purge control valve 8 and the split control valve 9 constitute a gas discharge opening and closing unit for opening and closing the gas discharge flow path, respectively.

In the present embodiment, as described above, the analysis can be performed while setting the whole flow rate control valve 7, the purge control valve 8, and the split control valve 9 in the open state, and the whole gas supply mode for introducing the whole amount of the carrier gas from the column inlet 31 can be executed. In the whole amount supply mode of gas, in a state in which the purge flow path 12 is closed by the purge control valve 8 and the split flow path 13 is closed by the split control valve 9, by opening the whole flow rate control valve 7, the carrier gas is supplied to the sample introduction unit 3 from the gas supply flow path 11. In this case, since the gas is not discharged to the outside via the purge flow path 12 or the split flow path 13, the entire carrier gas supplied to the sample introduction unit 3 is introduced from the column inlet 31.

Figure 2:
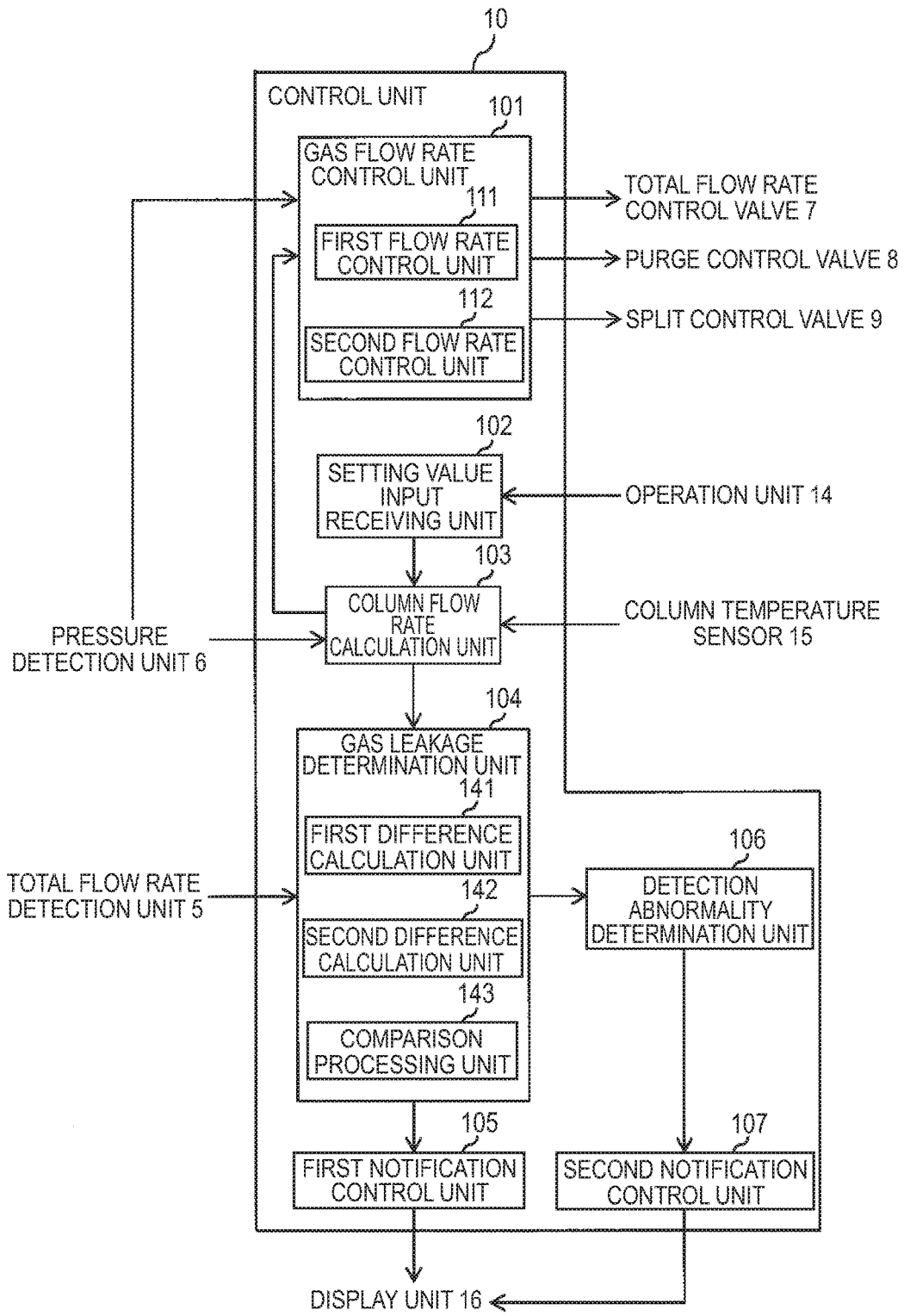
FIG. 2 is a block diagram illustrating an example of an electrical configuration in the gas chromatograph of FIG. 1.

FIG. 2 is a block diagram illustrating an example of an electrical configuration in the gas chromatograph of FIG. 1. The operation of the gas chromatograph is controlled, for example, by a control unit 10 including a central processing unit (CPU). By executing the program through the CPU, the control unit 10 serves as a gas flow rate control unit 101, a setting value input accepting unit 102, a column flow rate calculation unit 103, a gas leakage determination unit 104, a first notification control unit 105, a detection abnormality determination unit 106, a second notification control unit 107, and the like.

By opening and closing the whole flow rate control valve 7, the purge control valve 8 and the split control valve 9, the gas flow rate control unit 101 can supply the carrier gas into the column 1 from the column inlet 31 in various control modes. Examples of the control modes can include, for example, a constant pressure control, a constant linear velocity control, a constant flow rate control, and the like. The gas flow rate control unit 101 functions as a first flow rate control unit 111 and a second flow rate control unit 112.

In the present embodiment, the gas flow rate control unit 101 can execute the whole amount supply mode of gas, by performing the control to open the whole flow rate control valve 7 in a state in which the purge control valve 8 and the split control valve 9 are closed. The whole amount supply mode of gas is executed, for example, before the analysis. The whole amount supply mode of gas may be configured to be performed on the basis of an input operation of an operator or may be configured to be performed automatically.

The setting value input accepting unit 102 performs a process for receiving the input of the setting value from the operating unit 14. The operating unit 14 includes, for example, a keyboard or a mouse, and is configured so that an operator can perform an input operation by operating the operating unit 14. However, the setting value input accepting unit 102 is not limited to the input of the setting value from the operating unit 14, but may be configured to receive the input of the setting values in other modes, such as receiving the setting values transmitted from other devices.

In the present embodiment, it is possible to accept the input of the setting value concerning the column 1 by the setting value input accepting unit 102. As the setting values concerning the column 1, for example, the inner diameter and the length of column 1 and the film thickness of liquid phase can be exemplified. The setting value concerning the column 1 that accepts the input by the setting value input accepting unit 102 is input to the column flow rate calculation unit 103. However, the invention is not limited to such a configuration. For example, a configuration may be adopted in which the setting value concerning the column 1 that accepts the input by the setting value input accepting unit 102 is temporarily stored in a storage unit (not illustrated), is read from the storage unit, and is input to the column flow rate calculation unit 103.

The column flow rate calculation unit 103 calculates the column flow rate during the whole amount supply mode of gas, that is, when the whole amount of the carrier gas is introduced from the column inlet 31. Specifically, the column flow rate is calculated, on the basis of the column inlet pressure detected by the pressure detection unit 6, the setting value concerning the column 1 that accepts the input by the setting value input accepting unit 102, and the temperature of the column 1. Since the method for calculating the column flow rate based on these values is well known, the detailed description thereof will not be provided.

In the gas chromatograph according to this embodiment, a column temperature sensor 15 for detecting the temperature of the column 1 is provided, and the temperature (actually measured value) of the column 1 detected by the column temperature sensor 15 is used when calculating the gas flow rate. The column temperature sensor 15 is disposed, for example, in the column oven 2. However, for example, a configuration in which the temperature (Setting value) that accepts the input by the setting value input accepting unit 102 is used as the temperature of the column 1, without being limited to such a configuration.

During the whole amount supply mode of gas, the first flow rate control unit 111 controls the flow rate of the carrier gas supplied from the gas supply flow path 11, using the whole flow rate control valve 7, so that the column flow rate (column flow rate calculation value) calculated by the column flow rate calculation unit 103 becomes a predetermined first flow rate, on the basis of the column inlet pressure detected by the pressure detection unit 6. Further, the second flow rate control unit 112 controls the flow rate of the carrier gas supplied from the gas supply flow path 11 using the whole flow rate control valve 7, such that the column flow rate calculation value becomes a predetermined second flow rate different from the first flow rate, on the basis of the column inlet pressure detected by the pressure detection unit 6.

The gas leakage determination unit 104 determines the presence or absence of leakage of the carrier gas in the gas supply flow path 11 from the whole flow rate detection unit 5 to the sample introduction unit 3, on the basis of the flow rate of the carrier gas (whole flow rate detection value) detected by the whole flow rate detection unit 5. Specifically, the gas leakage determination unit 104 determines the presence or absence of leakage of the carrier gas, on the basis of the whole flow rate detection value (first whole flow rate detection value) when the flow rate of the carrier gas is controlled by the first flow rate control unit 111, the whole flow rate detection value (second whole flow rate detection value) when the flow rate of the carrier gas is controlled by the second flow rate control unit 112, the first flow rate, and the second flow rate.

That is, when the flow rate of the carrier gas calculated by the column flow rate calculation unit 103 is controlled to be the first flow rate, and when the flow rate of the carrier gas is controlled to be the second flow rate, the flow rate of the carrier gas is detected by the whole flow rate detection unit 5, respectively, and the presence or absence of the leakage of the carrier gas is determined on the basis of the whole flow rate detection value, the first flow rate, and the second flow rate. In this way, since the flow rate of the carrier gas changes and the whole flow rate detection value is used at different flow rates (the first flow rate and the second flow rate), it is possible to satisfactorily discriminate a case where the offset occurs in the whole flow rate detection value and a case where leakage of the carrier gas occurs. Thus, it is possible to satisfactorily determine the presence or absence of leakage of the carrier gas.

In the present embodiment, the gas leakage determination unit 104 functions as a first difference calculation unit 141, a second difference calculation unit 142, and a comparison processing unit 143. The first difference calculation unit 141 calculates the difference between the first whole flow rate detection value and the first flow rate when the flow rate of the carrier gas is controlled by the first flow rate control unit 111. The second difference calculation unit 142 calculates the difference between the second whole flow rate detection value and the second flow rate when the flow rate of the carrier gas is controlled by the second flow rate control unit 112.

Figure 3A:
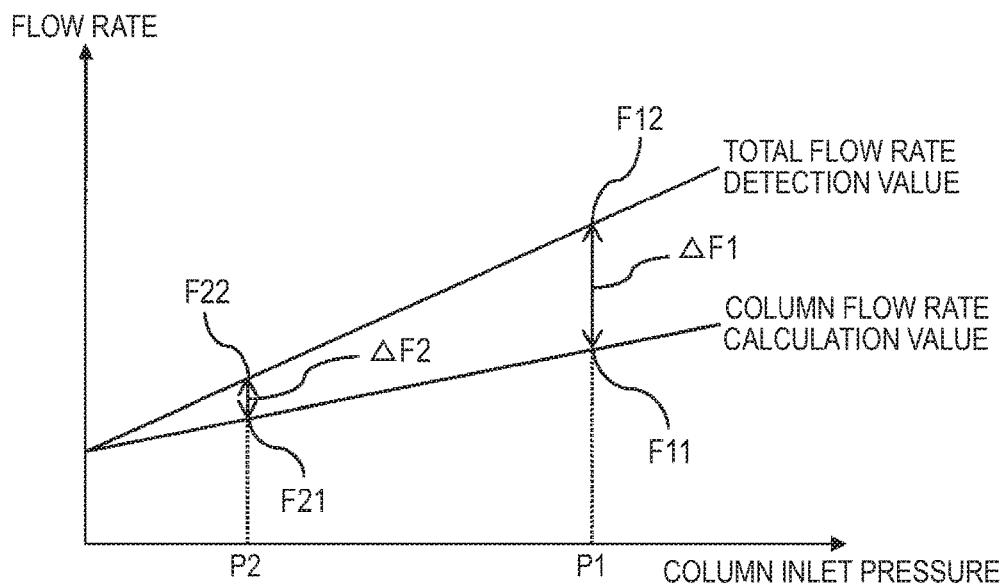
FIG. 3A is a diagram for describing a process performed by a first difference calculation unit and a second difference calculation unit, and illustrates a relation between a column flow rate calculation value and a whole flow rate detection value when leakage of the carrier gas occurs.
Figure 3B:
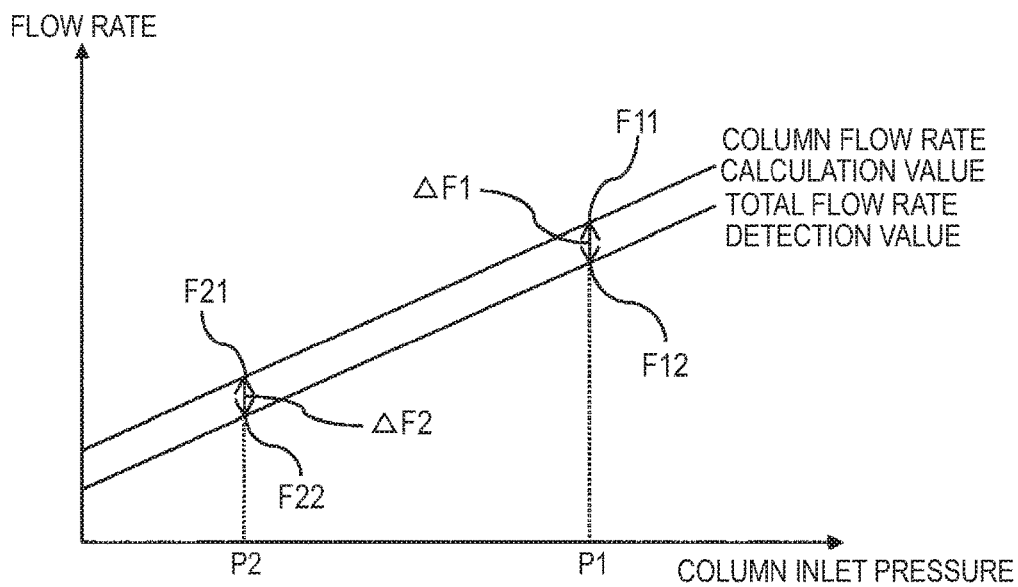
FIG. 3B is a diagram for describing a process performed by the first difference calculation unit and the second difference calculation unit, and illustrates a relation between the column flow rate calculation value and the whole flow rate detection value when the offset occurs in the whole flow rate detection value.

FIGS. 3A and 3B are diagrams for describing a process performed by the first difference calculation unit 141 and the second difference calculation unit 142. FIG. 3A illustrates a relation between the column flow rate calculation value and the whole flow rate detection value when the leakage of the carrier gas occurs, and FIG. 3B illustrates a relation between the column flow rate calculation value and the whole flow rate detection value when an offset occurs in the whole flow rate detection value, respectively.

As illustrated in FIG. 3A, when the leakage of the carrier gas occurs in the gas supply flow path 11 from the whole flow rate detection unit 5 to the sample introduction unit 3, if the flow rate of the carrier gas is large, the leakage amount with respect to the flow rate of the carrier gas is also relatively large. Therefore, as the column inlet pressure is high, the difference between the whole flow rate detection value and the column flow rate calculation value increases.

In this example, when a difference $\Delta F1$ between the column flow rate calculation value (first flow rate) F11 and a first whole flow rate detection value F12 at the column inlet pressure P1 is compared with a difference $\Delta F2$ between the column flow rate calculation value (second flow rate) F21 and a second whole flow rate detection value F22 at the column inlet pressure P2 lower than the column inlet pressure P1, the difference $\Delta F1$ is larger than the difference $\Delta F2$.

Meanwhile, as illustrated in FIG. 3B, when an offset occurs in the whole flow rate detection value, the offset amount of the whole flow rate detection value with respect to the column flow rate calculation value is substantially constant, irrespective of the flow rate of the carrier gas. In this example, the difference $\Delta F1$ between the column flow rate calculation value (first flow rate) F11 and the first whole flow rate detection value F12 at the column inlet pressure P1, and the difference $\Delta F2$ between the column flow rate calculation value (second flow rate) F21 and the second whole flow rate detection value F22 at the column inlet pressure P2 lower than the column inlet pressure P1 are substantially the same value.

The first difference calculation unit 141 calculates the difference $\Delta F1$ (=|F11−F12|). Further, the second difference calculation unit 142 calculates the difference $\Delta F2$ (=|F21−F22|). The comparison processing unit 143 illustrated in FIG. 2 performs the process of comparing the difference $|\Delta F1-\Delta F2|$ between the difference $\Delta F1$ calculated by the first difference calculation unit 141 and the difference $\Delta F2$ calculated by the second difference calculation unit 142 with the first threshold value.

In this way, in the present embodiment, the flow rate of the carrier gas changes, the whole flow rate detection values F12 and F22 at different flow rates (the first flow rate and the second flow rate) are acquired, and the difference $\Delta F1$ between the first whole flow rate detection value F12 and the first flow rate F11 at the first flow rate, and the difference $\Delta F2$ between the second whole flow rate detection value F22 and the second flow rate F21 at the second flow rate are calculated. As described above, when leakage of the carrier gas occurs, since the difference $\Delta F1$ is larger than the difference $\Delta F2$, the difference $|\Delta F1-\Delta F2|$ becomes relatively large. Therefore, by comparing the difference $|\Delta F1-\Delta F2|$ with the first threshold value, the presence or absence of leakage of the carrier gas can be satisfactorily determined. The first threshold value is, for example, about 10 ml/min, and may be set to a predetermined value in consideration of a manufacturing error or the like of the column 1, or may be set to an arbitrary value.

Referring again to FIG. 2, when the gas leakage determination unit 104 determines that there is leakage of the carrier gas, the first notification control unit 105 performs a process for notifying the leakage. Specifically, the first notification control unit 105 performs a notification by displaying the presence of leakage of the carrier gas on the display unit 16. The display unit 16 includes, for example, a liquid crystal display device or the like. The display unit 16 may be provided in the gas chromatograph itself or may be provided separately from the gas chromatograph.

As a result, after satisfactorily determining the presence or absence of leakage of the carrier gas, it is possible to notify the determination result thereof. Therefore, the operator can satisfactorily check the presence or absence of leakage of the carrier gas by clearly distinguishing from a case where an offset occurs in the whole flow rate detection value. However, the notification of the first notification control unit 105 is not limited to the configuration that is performed by the display on the display unit 16, and may be configured to be performed in another mode such as a voice.

When the gas leakage determination unit 104 determines that there is no leakage of the carrier gas, the detection abnormality determination unit 106 determines the presence or absence of detection abnormality in the whole flow rate detection unit 5. In the present embodiment, the detection abnormality determination unit 106 determines whether or not an offset of the whole flow rate detection value as illustrated in FIG. 3B occurs. Specifically, the difference $\Delta F2$ (=|F21−F22|) calculated by the second difference calculation unit 142 at the second flow rate F21, which is a smaller flow rate, is compared with the second threshold value, and when the difference $\Delta F2$ is equal to or higher than the second threshold value, it is determined that an offset of the whole flow rate detection value occurs.

As described above, in the present embodiment, in a case where it is determined that there is no leakage of the carrier gas after the satisfactory determination of presence or absence of the leakage of the carrier gas, by comparing the difference $\Delta F2$ calculated by the second difference calculation unit 142 with the second threshold value, the presence or absence of the detection abnormality in the whole flow rate detection unit 5 is determined. That is, when it is determined that there is no leakage of the carrier gas, if the difference $\Delta F2$ calculated by the second difference calculation unit 142 is large, there is a high possibility of occurrence of an offset in the whole flow rate detection value. Therefore, by comparing the difference $\Delta F2$ with the second threshold value, it is possible to satisfactorily determine the presence or absence of the detection abnormality in the whole flow rate detection unit 5. The second threshold value may be set to a predetermined value or may be set to an arbitrary value, in consideration of, for example, a manufacturing error or the like of the column 1.

When the detection abnormality determination unit 106 determines that there is a detection abnormality in the whole flow rate detection unit 5, the second notification control unit 107 performs a process for notifying the detection abnormality. Specifically, the second notification control unit 107 performs the notification by displaying the occurrence of the detection abnormality in the whole flow rate detection unit 5 on the display unit 16.

As a result, it is possible to notify the result of the determination after satisfactorily determining the presence or absence of the detection abnormality in the whole flow rate detection unit 5. Therefore, the operator can satisfactorily check the detection abnormality such as the occurrence of the offset in the whole flow rate detection value by clearly distinguishing from a case where the leakage of the carrier gas occurs. However, the notification of the second notification control unit 107 is not limited to the configuration that is performed by the display on the display unit 16, and may be configured to be performed in another mode such as voice.

Figure 4B:
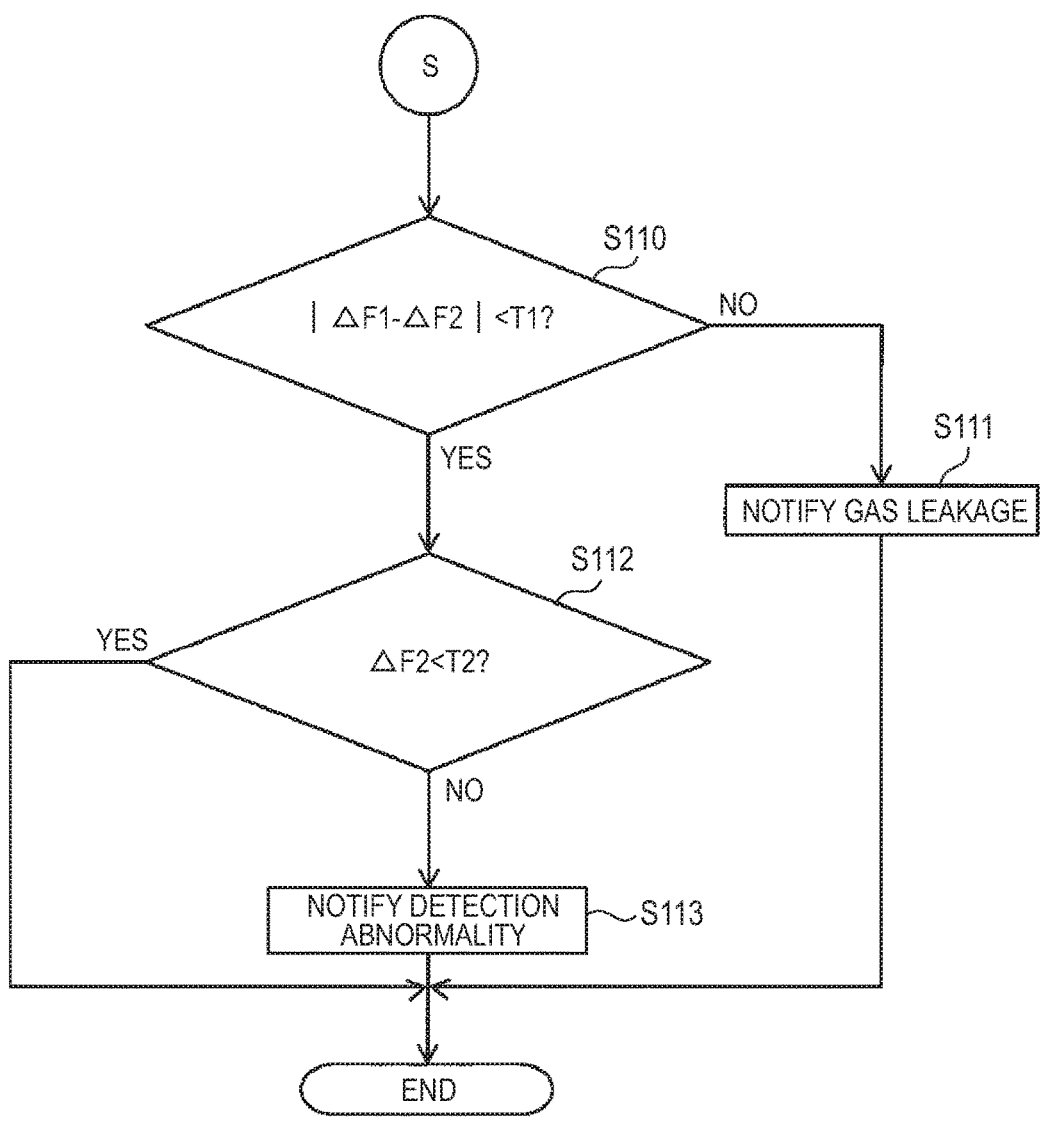
FIG. 4B is a flowchart illustrating an example of a process performed by the control unit when executing a whole amount supply mode of gas.

FIGS. 4A and 4B are flowcharts illustrating an example of a process performed by the control unit 10 when executing the whole amount supply mode of gas. In the whole amount supply mode of gas, when the purge control valve 8 and the split control valve 9 are in a closed state (Steps S101 and S102), by setting the whole flow rate control valve 7 in the open state (Step S103), the whole amount of the carrier gas is introduced into the column 1 from the column inlet 31.

In this state, the flow rate of the carrier gas is controlled by the first flow rate control unit 111 so that the flow rate of the carrier gas calculated by the column flow rate calculation unit 103 becomes the first flow rate F11 (Step S104). At this time, the first whole flow rate detection value F12 is acquired by the whole flow rate detection unit 5 (Step S105), and the first difference calculation unit 141 calculates the difference $\Delta F1=|F11-F12|$ (Step S106).

Next, the flow rate of the carrier gas is controlled by the second flow rate control unit 112 so that the flow rate of the carrier gas calculated by the column flow rate calculation unit 103 becomes the second flow rate F21 (Step S107). At this time, the second whole flow rate detection value F22 is acquired by the whole flow rate detection unit 5 (Step S108), and the second difference calculation unit 142 calculates the difference $\Delta F2=|F21-F22|$ (Step S109).

Further, the comparison processing unit 143 compares the difference $|\Delta F1-\Delta F2|$ between the difference $\Delta F1$ calculated by the first difference calculation unit 141 and the difference $\Delta F2$ calculated by the second difference calculation unit 142 with the first threshold value T1 (Step S110). As a result, if $|\Delta F1-\Delta F2|\geq T1$ (No in step S110), the gas leakage determination unit 104 determines that there is a leakage of the carrier gas, and the first notification control unit 105 notifies the leakage of carrier gas, using the display unit 16 (Step S111).

Meanwhile, in the case of $|\Delta F1-\Delta F2|<T1$ (Yes in step S110), the gas leakage determination unit 104 determines that there is no leakage of the carrier gas, and the difference $\Delta F2$ calculated by the second difference calculation unit 142 is compared with the second threshold value T2. As a result, if $\Delta F2\geq T2$ (No in step S112), the detection abnormality determination unit 106 determines that an offset of the whole flow rate detection value occurs, and the second notification control unit 107 notifies the detection abnormality, using the display unit 16 (Step S113). In contrast, if $\Delta F2<T2$ (Yes in step S112), the detection abnormality determination unit 106 determines that an offset of the whole flow rate detection value does not occur, and the notification of the first notification control unit 105 and the second notification control unit 107 is not performed.

Figure 5:
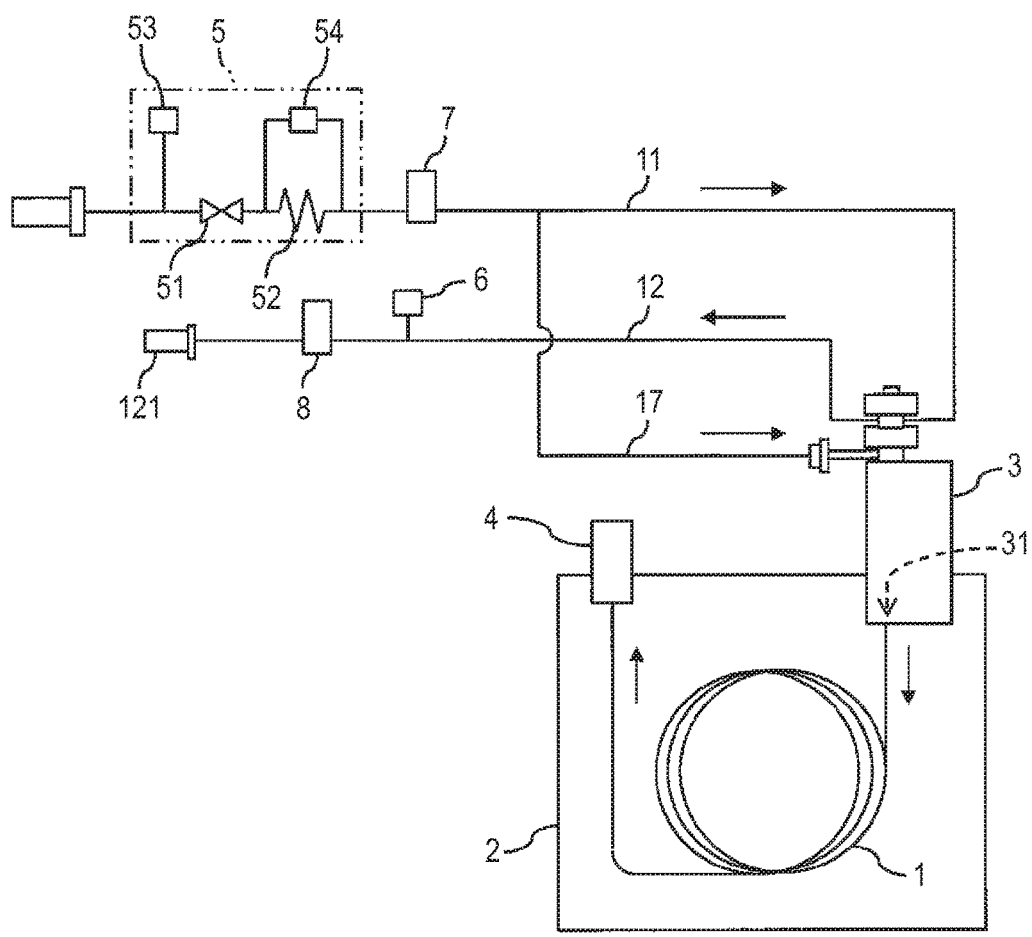
FIG. 5 is a schematic view illustrating a configuration example of a gas chromatograph according to another embodiment.
Figure 6A:
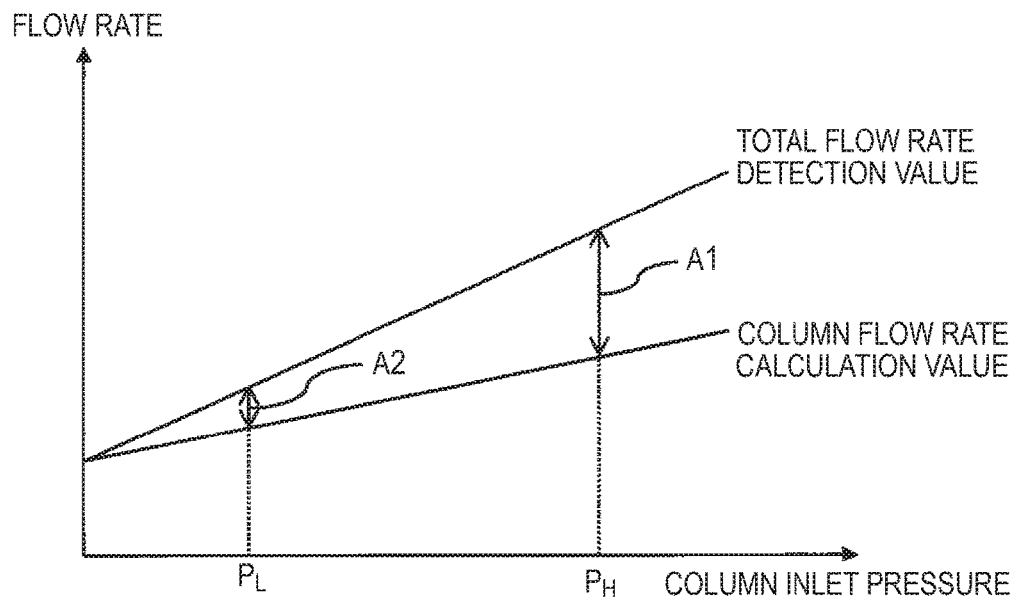
FIG. 6A is a diagram for describing a relation between a column flow rate calculation value and a whole flow rate detection value, and illustrates a case where leakage of the carrier gas occurs.
Figure 6B:
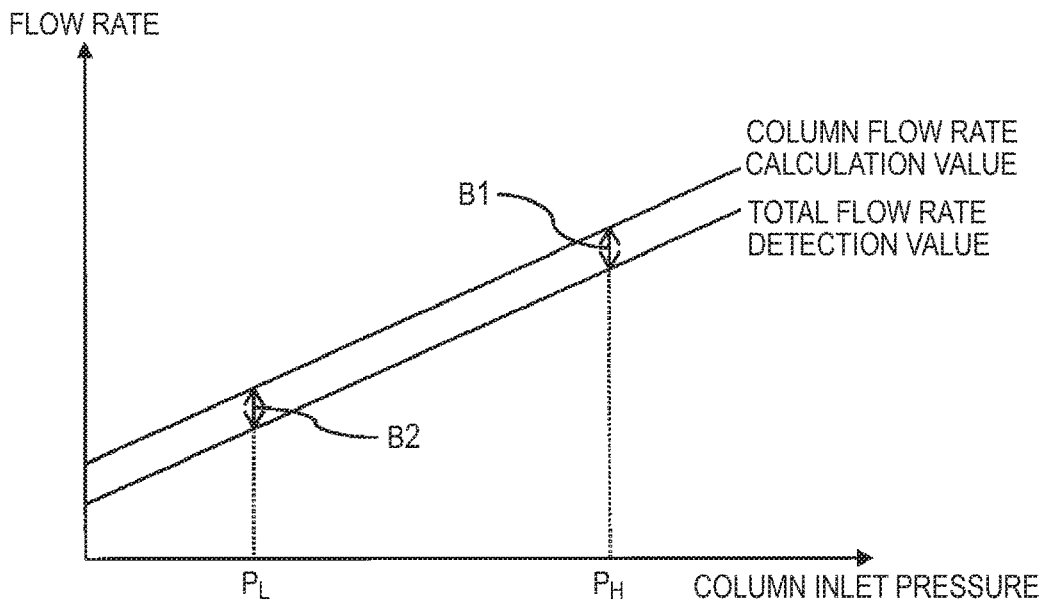
FIG. 6B is a diagram for describing a relation between a column flow rate calculation value and a whole flow rate detection value, and illustrates a case where an offset occurs in the whole flow rate detection value.

FIG. 5 is a schematic view illustrating a configuration example of a gas chromatograph according to another embodiment. The gas chromatograph is configured to introduce the carrier gas into the column 1 from the column inlet 31 by a whole amount introduction method, rather than the split introduction method as described in the above embodiment.

Specifically, the split flow path 13 is not provided in the gas chromatograph according to the present embodiment, and a branch path 17 branched from the middle part of the gas supply flow path 11 is connected to a portion of the sample introduction unit 3 to which the split flow path 13 is connected. This makes it possible to supply the carrier gas from both of the gas supply flow path 11 and the branch path 17 into the sample introduction unit 3 such that an occurrence of a dead volume can be prevented. However, a configuration in which the branch path 17 is omitted may be provided.

In this way, the gas chromatograph according to the present embodiment does not have the split flow path 13. Therefore, the gas discharge flow path for discharging a part of the gas in the sample introduction unit 3 during the analysis is constituted only by the purge flow path 12. In this way, the number of the gas discharge flow paths may be one rather than two. Further, a configuration in which three or more gas discharge flow paths are provided may be adopted.

Since the gas chromatograph according to this embodiment has the same configuration as that of the above embodiment except that the split flow path 13 is not provided, the same configurations are denoted by the same reference numerals, and the detailed thereof will not be provided.

As described above, the invention can also be applied to a configuration in which the carrier gas is introduced into the column 1 from the column inlet 31 by one of the split introduction method and the whole amount introduction method. Further, the invention can also be applied to a configuration in which the carrier gas is introduced into the column 1 from the column inlet 31 by another method, without being limited to the split introduction method and the whole amount introduction method.

The above embodiment illustrates the configuration in which the gas leakage determination unit 104 determines the presence or absence of leakage of the carrier gas by comparing the difference |ΔF1−ΔF2| with the first threshold value T1, using the whole flow rate detection value at each flow rate. However, the gas leakage determination unit 104 can also determine the presence or absence of leakage of the carrier gas by other various processes, without being limited to such a configuration.

Further, the above embodiment illustrates the configuration in which the flow rate of the carrier gas is changed to two different flow rates (the first flow rate and the second flow rate), and the presence or absence of leakage of the carrier gas is determined using the whole flow rate detection value at each flow rate. However, for example, a configuration may be provided in which the flow rate of the carrier gas is changed to three or more different flow rates, and the presence or absence of the leakage of the carrier gas is determined using the whole flow rate detection value at those flow rates, without being limited to such a configuration.

Further, the above embodiment illustrates the configuration in which the detection abnormality determination unit 106 determines the presence or absence of the offset of the whole flow rate detection value, by comparing the difference ΔF2 (=|F21−F22|) calculated by the second difference calculation unit 142 at the second flow rate F21 with the second threshold value. However, the detection abnormality determination unit 106 may be configured to determine the presence or absence of the offset of the whole flow rate detection value, on the basis of the difference between the column flow rate calculation value calculated at the flow rate other than the second flow rate F21 and the whole flow rate detection value, without being limited thereto.

In the above embodiment, the configuration in which the liquid sample is vaporized in the sample introduction unit 3 (sample vaporization chamber) has been described. However, the invention is not limited to such a configuration, and the already vaporized sample gas may be supplied into the sample introduction unit 3. In this case, it may not be necessary to have a configuration in which a sample vaporization chamber is formed inside the sample introduction unit 3.

What is claimed is:

1. A gas chromatograph comprising:
   a column into which a sample is introduced from a column inlet;
   a sample introduction unit which introduces the sample together with a carrier gas into the column from the column inlet;
   a gas supply unit which communicates with the sample introduction unit to supply a carrier gas to the sample introduction unit;
   a whole flow rate detection unit which detects a flow rate of the carrier gas supplied from the gas supply unit;
   a pressure detection unit which detects a pressure of the carrier gas at the column inlet;
   a column flow rate calculation unit which calculates a flow rate of the carrier gas passing through the column, on the basis of the pressure of the carrier gas at the column inlet;
   a first flow rate control unit which controls the flow rate of the carrier gas supplied from the gas supply unit so that the flow rate of the carrier gas calculated by the column flow rate calculation unit becomes a first flow rate;
   a second flow rate control unit which controls the flow rate of the carrier gas supplied from the gas supply unit so that the flow rate of the carrier gas calculated by the column flow rate calculation unit becomes a second flow rate different from the first flow rate; and
   a gas leakage determination unit which determines presence or absence of leakage of the carrier gas, on a basis of the flow rate of the carrier gas detected by the whole flow rate detection unit when the flow rate of the carrier gas is controlled by the first flow rate control unit, the flow rate of the carrier gas detected by the whole flow rate detection unit when the flow rate of the carrier gas is controlled by the second flow rate control unit, the first flow rate, and the second flow rate.

2. The gas chromatograph according to claim 1, wherein the gas leakage determination unit includes:
   a first difference calculation unit which calculates a difference between the flow rate of the carrier gas detected by the whole flow rate detection unit when the flow rate of the carrier gas is controlled by the first flow rate control unit and the first flow rate;
   a second difference calculation unit which calculates a difference between the flow rate of the carrier gas detected by the whole flow rate detection unit when the flow rate of the carrier gas is controlled by the second flow rate control unit and the second flow rate; and
   a comparison processing unit which compares a difference between the difference calculated by the first difference calculation unit and the difference calculated by the second difference calculation unit with a first threshold value.

3. The gas chromatograph according to claim 1, further comprising:
   a first notification control unit which notifies the leakage, when the gas leakage determination unit determines that there is leakage of the carrier gas.

4. The gas chromatograph according to claim 1, further comprising:
   a detection abnormality determination unit which determines presence or absence of a detection abnormality in the whole flow rate detection unit, by comparing the difference calculated by the first difference calculation unit or the second difference calculation unit with a second threshold value, when the gas leakage determination unit determines that there is no leakage of the carrier gas.

5. The gas chromatograph according to claim 4, further comprising:
a second notification control unit which notifies detection abnormality, when the detection abnormality determination unit determines that there is a detection abnormality in the whole flow rate detection unit.

6. The gas chromatograph according to claim 2, further comprising:
a first notification control unit which notifies the leakage, when the gas leakage determination unit determines that there is leakage of the carrier gas.

7. The gas chromatograph according to claim 2, further comprising:
a detection abnormality determination unit which determines presence or absence of a detection abnormality in the whole flow rate detection unit, by comparing the difference calculated by the first difference calculation unit or the second difference calculation unit with a second threshold value, when the gas leakage determination unit determines that there is no leakage of the carrier gas.

8. The gas chromatograph according to claim 3, further comprising:
a detection abnormality determination unit which determines presence or absence of a detection abnormality in the whole flow rate detection unit, by comparing the difference calculated by the first difference calculation unit or the second difference calculation unit with a second threshold value, when the gas leakage determination unit determines that there is no leakage of the carrier gas.

* * * * *